United States Patent [19]

Nietupski

[11] Patent Number: 4,521,427

[45] Date of Patent: Jun. 4, 1985

[54] APPETITE SUPPRESSANT AND METHOD OF APPLICATION THEREOF

[76] Inventor: Ronald S. Nietupski, 16500 Spaniel Dr., Lockport, Ill. 60441

[21] Appl. No.: 495,436

[22] Filed: May 17, 1983

[51] Int. Cl.$^3$ ............................................. A61K 31/44
[52] U.S. Cl. .................................................... 514/354
[58] Field of Search ......................................... 424/263

[56] References Cited

PUBLICATIONS

Chemical Abstracts; vol. 75, (1971); Walradt et al., #108666J.

Chemical Abstracts; vol. 75, (1971); Buttery et al., #108670f.

Organic Chemistry; vol. II, 2nd Edition, p. 781; F. C. Whitmore.

*Primary Examiner*—Leonard Schenkman
*Assistant Examiner*—Joseph A. Lipovsky
*Attorney, Agent, or Firm*—Todd S. Parkhurst

[57] ABSTRACT

A method for suppressing the appetite of an individual is disclosed. The method comprises inhaling an effective amount of a volatile appetite suppressant for neutralizing olfactory stimulus, thereby suppressing appetite. Also disclosed is a device for presenting or applying the suppressant.

5 Claims, 4 Drawing Figures

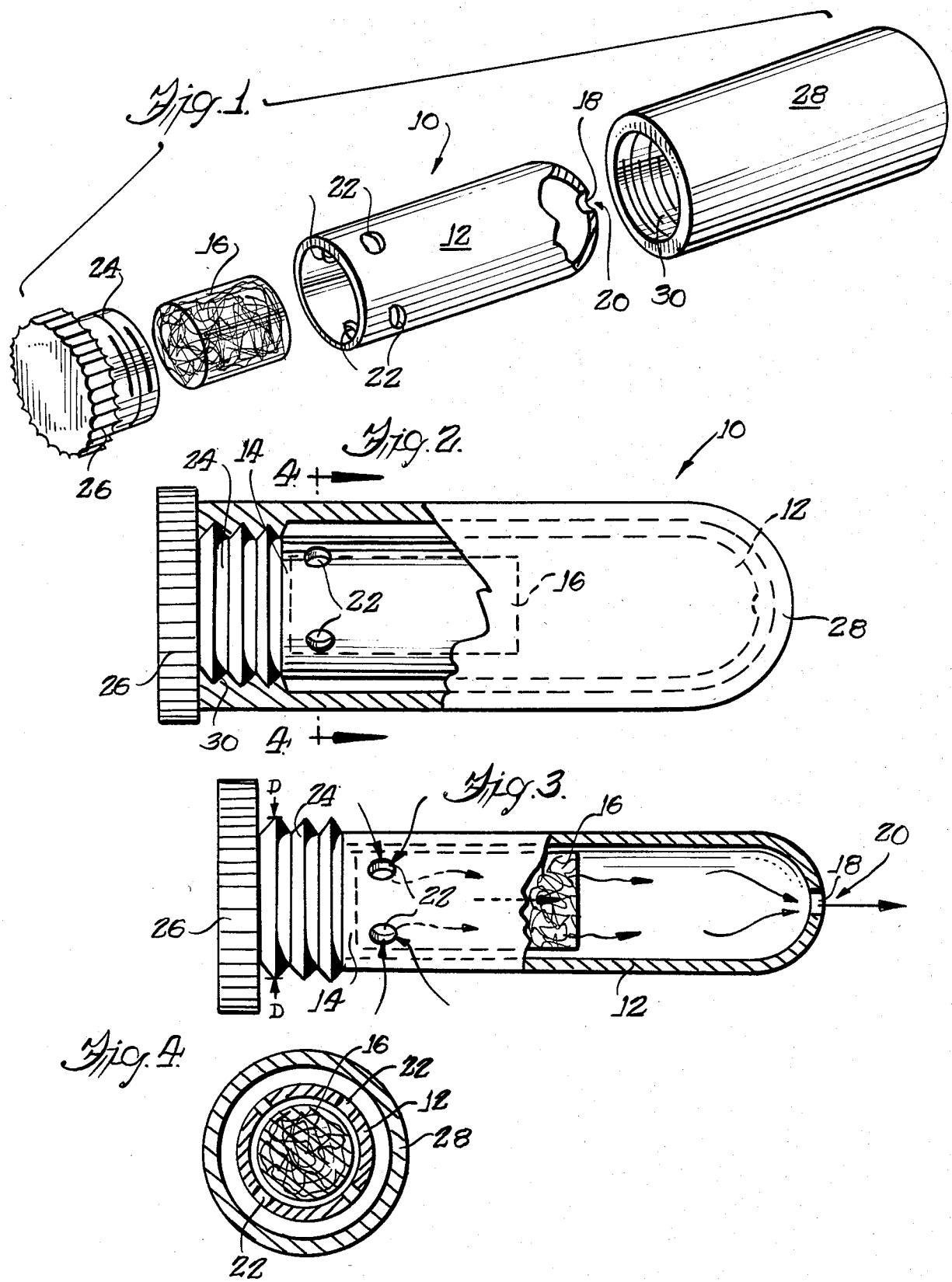

4,521,427

APPETITE SUPPRESSANT AND METHOD OF APPLICATION THEREOF

BACKGROUND OF THE INVENTION

This invention is directed to a novel appetite suppressant. More particularly, this invention is directed to a novel suppressant, a method of applying the appetite suppressant, and an inhaler for the suppressant.

Dieting aids are well known. Most of these are taken orally. Some dieting aids are ineffective under certain conditions, and some aids can often be harmful to the user.

OBJECTS AND SUMMARY OF THE INVENTION

Accordingly, it is a general object of this invention to provide, to the consumer, an appetite suppressant which is novel in nature and effective in use.

A more specific object is to provide such an appetite suppressant which can be inhaled.

A related object is to provide an inhaler device for presenting or offering the appetite suppressant.

Briefly, and in accordance with the foregoing objects, a novel method for suppressing the appetite of an individual is described. This method comprises inhaling an effective amount of a volatile appetite suppressant, so as to neutralize olfactory stimulus and thereby suppress appetite. Preferably, the suppressant is an odorant having an intensity which matches 10–500 ppm (volume/volume) of 1-butanol.

BRIEF DESCRIPTION OF THE DRAWING

Other objects and advantages of the invention will become apparent upon reading the following detailed description and upon reference to the drawings, in which:

FIG. 1 is an exploded view of the appetite suppressant inhaler;

FIG. 2 is a side or top view, in partial section, of the cylindrical inhaler;

FIG. 3 is a side or top view, in partial section, of a suppressant-substance-containing tube; and FIG. 4 is a sectional view taken substantially in the plane of line 4—4 in FIG. 2.

Throughout the drawings, like reference numerals refer to like parts

DETAILED DESCRIPTION OF THE ILLUSTRATED EMBODIMENT

An appetite-suppressing inhaler 10 is shown in FIG. 1. The inhaler or device 10 comprises an elongated tube 12 having an end closure 14. The tube 12 surrounds a support means 16 onto which the appetite suppressant is impregnated. The support means 16 can be paraffin, gauze or the like. The tube 12 includes a through outlet aperture 18 adjacent an inhalation zone or region 20 set apart from the support means 16. A plurality of (preferably four) circumferentially-spaced through inlet apertures 22 are proximate to the end closure 14. Those apertures 18, 22 permit an individual user to draw air into the tube 12 via the inlet apertures 22, across the support means 16 and out the outlet aperture 18 (FIG. 3). The volatile suppressant is transferred from the support means 16 and into the air. Air being drawn across the support means 16 picks up suppressant vapors and transfers these vapors to the inhalation zone or region 20, whereby the individual can inhale the vapors for suppressing appetite.

The tube 12 preferably further includes circumferential threads 24 formed integral with the end closure 14 and in distal relation to the outlet orifice 18, and a knurled end 26, preferably circular in cross section. The end 26 has a diameter which is greater than that of the tube 12, and greater than the outer diameter D (FIG. 3) of the threads 24. It can be appreciated that the threads 24 and end 26 permit the tube 12 to be screwed into a second tube or closure 28 open only at a threaded end. So closing the inhaler 10 curtails undesired volatilization of the appetite suppressant from the support means 16. The second tube 28 preferably includes integral threads 30 (FIGS. 1 and 2) which mesh with the threads 24 so as to accomplish this purpose.

THE APPETITE SUPPRESSANT

It is well known that moisture is a vehicle which delivers molecular odor perception to olfactory receptors of an individual; those receptors are located at the very top of the nasal cavity near the inner end of the person's upper throat. I have found that such receptors can trigger appetite suppression, and that any odor which is non-food-, flower- or sweet-related generally curbs ones immediate desire to eat.

I have further found that a dry nose and tongue are incapable of detecting substantial amounts of smell or taste. Consequently, it appears that substances which slightly and harmlessly dry the nose and tongue will act as appetite suppressants when they are inhaled.

In addition, I have discovered that repeated inhalation of these odors or substances appears to have an appetite-suppressing psychological or conditioning effect. For example, after repeated use of my invention, simply deciding to reach for, or simply touching the inhaler can trigger the appetite suppression effect.

I have tested a number of inhalant substances as appetite suppressants. These suppressants tested are presented below in Table I.

TABLE I

| APPETITE SUPPRESSANT | | CONCENTRATION OF ACTIVE INGREDIENT PER LITER OF DIPROPYLENE GLYCOL |
|---|---|---|
| NO. | ACTIVE INGREDIENT | |
| 1 | Camphor | 20 g |
| 2 | Amylbutyrate | 20 ml |
| 3 | Methyl anthranilate | 20 ml |
| 4 | Methylsalycilate | 20 ml |
| 5 | Eucaliptol | 20 ml |
| 6 | Tetraquinone | 50 g |
| 7 | Tonalid Musk | 5 g |
| 8 | 2-Acetylpyridine | 10 ml |
| 9 | Isopropylquinoline | 10 ml |
| 10 | Thymol | 100 g |
| 11 | Dimethyltrisulfide | 10 g. |
| 12 | 2-Ethylpyrazine | 40 ml |

Mixing of the appetite suppressant with air can be achieved in a variety of ways. For example, mixing can be achieved by placing the appetite suppressant in an enclosure supplied with an opening which restricts the rate at which vaporized appetite suppressant escapes from the enclosure. The rate can also be restricted by a porous or non-porous, but vapor-permeable, membrane.

It is currently standard procedure to match odor intensity to 1-butanol. This procedure is outlined in ASTM E 544. The appetite suppressants presented in Table I were tested in accordance with ASTM E 544

(see Tables II–XIII). I have found that odor intensities which match, preferably, 10–500 ppm (volume/volume) of 1-butanol are useful for suppressing appetite in humans. Odor intensities less than those matching 10 ppm of 1-butanol are generally too weak, except for very sensitive individuals. Odor intensities matching more than 500 ppm 1-butanol are quite strong, and generally appear to be needed only by individuals who are rather insensitive to a particular suppressant.

Odor intensity of a suppressant is affected by the solvent into which the suppressant is diluted. It is desirable to use a solvent which has substantially no odor of its own. In addition, it is desirable to use a solvent which does not modify the odor of the suppressant, and which is not toxic or irritating to skin and mucous membranes. It is also desirable that the solvent be chemically unreactive with the suppressant. Dipropylene glycol (Table I) was used as the solvent because it meets these prerequisites, and also because it dissolves both water- and oil-soluble suppressants. Other solvents or diluents may be effective, as well.

USE OF THE DEVICE

The appetite suppressant can be presented to the user or consumer by the handy inhaler 10. During use, outlet aperture 18 is positioned proximate to the nostrils of an individual, and the individual inhales. This causes air to be drawn into the inlet apertures 22, across the support means 16 and out the outlet aperture 18. This passage of air across the support means 16 causes the suppressant to vaporize and to be transported from the support means 16 to the inhalation zone or region 20. From the region 20 the vapors are drawn by the individual user via the nostrils to the olfactory receptors. The quantity of suppressant thus inhaled by an individual is subjective and generally varies from one individual to another.

TESTING OF THE SUPPRESSANT

A standarized test was used to evaluate appetite suppression characteristics of the suppressants presented in Table I. This method is outlined in ASTM Special Technical Publication (STP) No. 434 at pages 50 and 51. Briefly, in a number of individuals, two subjective sensory stimuli were tested. The stimuli were hunger sensations. The first stimulus was a ranked hunger sensation recorded before inhaling the suppressant. The second stimulus was a ranked hunger sensation recorded after inhaling the suppressant. The two sensations were then compared for a number of individuals, using a rating scale. The procedure of STP No. 434 was used to determine if the difference between any two matched or paired stimuli could be attributable simply to chance, or whether such differences were otherwise statistically significant. The 95% confidence level was used to test statistical significance. The 95% confidence level is used in many sensory evaluations by medical and psychological studies, and is considered sufficient by those in the medical and psychological areas for supporting claims to noted differences.

Twelve suppressants were tested. Each suppressant was tested upon six different individuals. The results of these tests are presented below in Tables II–XIII.

In each table, a numerical scale is used in which 5 represents the greatest hunger sensation, and 0 represents the least hunger or non-hunger sensation. "T" is a calculated statistical value which is arrived at by applying the experimental data of each one of the Tables II–XIII to a statistical formula, which is referred to as a T-distribution. (See, for example, *PROBABILITY AND STATISTICS FOR ENGINEERS AND SCIENTISTS*, by R. E. Walpole and R. H. Myers, published by the Macmillan Company of New York, New York, 1972, at pages 168–173 and 460.) The calculated value of T is then compared to a tabulated, critical value of T for determining whether the experimental data is or is not statistically significant at a preselected confidence level.

TABLE II

| | Suppressant* No. 1 HUNGER SCORE | | | |
|---|---|---|---|---|
| SUBJECT # | BEFORE | AFTER | DIFFERENCE | SQUARE OF DIFFERENCE |
| 1 | 3 | 1 | −2 | 4 |
| 2 | 4 | 2 | −2 | 4 |
| 3 | 2 | 2 | 0 | 0 |
| 4 | 4 | 4 | 0 | 0 |
| 5 | 0 | 0 | 0 | 0 |
| 6 | 3 | 1 | −2 | 4 |
| MEAN: | 2.67 | 1.67 | — | — |
| SUM: | — | — | −6 | 12 |
| T= | | | | −2.24** |

*Suppressant suppressed hunger . . . True
**Confidence level for this conclusion below 95%

TABLE III

| | Suppressant* No. 2 HUNGER SCORE | | | |
|---|---|---|---|---|
| SUBJECT # | BEFORE | AFTER | DIFFERENCE | SQUARE OF DIFFERENCE |
| 1 | 2 | 2 | 0 | 0 |
| 2 | 3 | 3 | 0 | 0 |
| 3 | 3 | 4 | 1 | 1 |
| 4 | 2 | 2 | 0 | 0 |
| 5 | 1 | 1 | 0 | 0 |
| 6 | 0 | 0 | 0 | 0 |
| MEAN: | 1.83 | 2.00 | — | — |
| SUM: | — | — | 1 | 1 |
| T= | | | | 1.00** |

*Suppressant suppressed hunger . . . False
**Confidence level for this conclusion very low

TABLE IV

| | Suppressant* No. 3 HUNGER SCORE | | | |
|---|---|---|---|---|
| SUBJECT # | BEFORE | AFTER | DIFFERENCE | SQUARE OF DIFFERENCE |
| 1 | 2 | 1 | −1 | 1 |
| 2 | 3 | 3 | 0 | 0 |
| 3 | 1 | 1 | 0 | 0 |
| 4 | 1 | 2 | 1 | 1 |
| 5 | 2 | 1 | −1 | 1 |
| 6 | 0 | 0 | 0 | 0 |
| MEAN: | 1.50 | 1.33 | — | — |
| SUM: | — | — | −1 | 3 |
| T= | | | | −0.54** |

*Suppressant suppressed hunger . . . True
**Confidence level for this conclusion very low

TABLE V

| | Suppressant* No. 4 HUNGER SCORE | | | |
|---|---|---|---|---|
| SUBJECT # | BEFORE | AFTER | DIFFERENCE | SQUARE OF DIFFERENCE |
| 1 | 4 | 3 | −1 | 1 |
| 2 | 3 | 2 | −1 | 1 |
| 3 | 2 | 3 | 1 | 1 |
| 4 | 5 | 4 | −1 | 1 |
| 5 | 1 | 1 | 0 | 0 |

TABLE V-continued

Suppressant* No. 4

| SUBJECT # | HUNGER SCORE BEFORE | HUNGER SCORE AFTER | DIFFERENCE | SQUARE OF DIFFERENCE |
|---|---|---|---|---|
| 6 | 2 | 0 | −2 | 4 |
| MEAN: | 2.83 | 2.17 | — | — |
| SUM: | — | — | −4 | 8 |
| T= | | | | −1.58** |

*Suppressant suppressed hunger . . . True
**Confidence level for this conclusion below 90%

TABLE VI

Suppressant* No. 5

| SUBJECT # | HUNGER SCORE BEFORE | HUNGER SCORE AFTER | DIFFERENCE | SQUARE OF DIFFERENCE |
|---|---|---|---|---|
| 1 | 3 | 0 | −3 | 9 |
| 2 | 3 | 1 | −2 | 4 |
| 3 | 3 | 3 | 0 | 0 |
| 4 | 4 | 3 | −1 | 1 |
| 5 | 3 | 2 | −1 | 1 |
| 6 | 4 | 2 | −2 | 4 |
| MEAN: | 3.33 | 1.83 | — | — |
| SUM: | — | — | −9 | 19 |
| T= | | | | −3.50** |

*Suppressant suppressed hunger . . . True
**Confidence level for this conclusion above 98%

TABLE VII

Suppressant* No. 6

| SUBJECT # | HUNGER SCORE BEFORE | HUNGER SCORE AFTER | DIFFERENCE | SQUARE OF DIFFERENCE |
|---|---|---|---|---|
| 1 | 3 | 1 | −2 | 4 |
| 2 | 3 | 2 | −1 | 1 |
| 3 | 5 | 5 | 0 | 0 |
| 4 | 4 | 4 | 0 | 0 |
| 5 | 2 | 2 | 0 | 0 |
| 6 | 5 | 2 | −3 | 9 |
| MEAN: | 3.67 | 2.67 | — | — |
| SUM: | — | — | −6 | 14 |
| T= | | | | −1.94** |

*Suppressant suppressed hunger . . . True
**Confidence level for this conclusion below 90%

TABLE VIII

Suppressant* No. 7

| SUBJECT # | HUNGER SCORE BEFORE | HUNGER SCORE AFTER | DIFFERENCE | SQUARE OF DIFFERENCE |
|---|---|---|---|---|
| 1 | 2 | 2 | 0 | 0 |
| 2 | 3 | 3 | 0 | 0 |
| 3 | 1 | 1 | 0 | 0 |
| 4 | 2 | 2 | 0 | 0 |
| 5 | 0 | 0 | 0 | 0 |
| 6 | 2 | 1 | −1 | 1 |
| MEAN: | 1.67 | 1.50 | — | — |
| SUM: | — | — | −1 | 1 |
| T= | | | | −1.00** |

*Suppressant suppressed hunger . . . True
**Confidence level for this conclusion very low

TABLE IX

Suppressant* No. 8

| SUBJECT # | HUNGER SCORE BEFORE | HUNGER SCORE AFTER | DIFFERENCE | SQUARE OF DIFFERENCE |
|---|---|---|---|---|
| 1 | 3 | 0 | −3 | 9 |
| 2 | 4 | 1 | −3 | 9 |
| 3 | 2 | 1 | −1 | 1 |

TABLE IX-continued

Suppressant* No. 8

| SUBJECT # | HUNGER SCORE BEFORE | HUNGER SCORE AFTER | DIFFERENCE | SQUARE OF DIFFERENCE |
|---|---|---|---|---|
| 4 | 3 | 2 | −1 | 1 |
| 5 | 1 | 1 | 0 | 0 |
| 6 | 4 | 2 | −2 | 4 |
| MEAN: | 2.83 | 1.17 | — | — |
| SUM: | — | — | −10 | 24 |
| T= | | | | −3.37** |

*Suppressant suppressed hunger . . . True
**Confidence level for this conclusion above 98%

TABLE X

Suppressant* No. 9

| SUBJECT # | HUNGER SCORE BEFORE | HUNGER SCORE AFTER | DIFFERENCE | SQUARE OF DIFFERENCE |
|---|---|---|---|---|
| 1 | 2 | 1 | −1 | 1 |
| 2 | 4 | 3 | −1 | 1 |
| 3 | 2 | 1 | −1 | 1 |
| 4 | 2 | 1 | −1 | 1 |
| 5 | 1 | 1 | 0 | 0 |
| 6 | 2 | 2 | 0 | 0 |
| MEAN: | 2.17 | 1.50 | — | — |
| SUM: | — | — | −4 | 4 |
| T= | | | | −3.16** |

*Suppressant suppressed hunger . . . True
**Confidence level for this conclusion above 95%

TABLE XI

Suppressant* No. 10

| SUBJECT # | HUNGER SCORE BEFORE | HUNGER SCORE AFTER | DIFFERENCE | SQUARE OF DIFFERENCE |
|---|---|---|---|---|
| 1 | 5 | 4 | −1 | 1 |
| 2 | 3 | 2 | −1 | 1 |
| 3 | 0 | 0 | 0 | 0 |
| 4 | 0 | 0 | 0 | 0 |
| 5 | 1 | 1 | 0 | 0 |
| 6 | 2 | 2 | 0 | 0 |
| MEAN: | 1.83 | 1.50 | — | — |
| SUM: | — | — | −2 | 2 |
| T= | | | | −1.58** |

*Suppressant suppressed hunger . . . True
**Confidence level for this conclusion below 90%

TABLE XII

Suppressant* No. 11

| SUBJECT # | HUNGER SCORE BEFORE | HUNGER SCORE AFTER | DIFFERENCE | SQUARE OF DIFFERENCE |
|---|---|---|---|---|
| 1 | 1 | 0 | −1 | 1 |
| 2 | 4 | 0 | −4 | 16 |
| 3 | COULD NOT OPEN INHALER | | 0 | 0 |
| 4 | COULD NOT OPEN INHALER | | 0 | 0 |
| 5 | 0 | 0 | 0 | 0 |
| 6 | COULD NOT OPEN INHALER | | 0 | 0 |
| MEAN: | 1.67 | — | — | — |
| SUM: | — | — | −5 | 17 |
| T= | | | | NOT AVAILABLE** |

*Suppressant suppressed hunger . . . No conclusion
**Confidence level for this conclusion: None

TABLE XIII

| | Suppressant* No. 12 | | | |
| | HUNGER SCORE | | | |
| SUBJECT # | BEFORE | AFTER | DIFFERENCE | SQUARE OF DIFFERENCE |
|---|---|---|---|---|
| 1 | 3 | 2 | −1 | 1 |
| 2 | 4 | 3 | −1 | 1 |
| 3 | 1 | 1 | 0 | 0 |
| 4 | 0 | 0 | 0 | 0 |
| 5 | 2 | 2 | 0 | 0 |
| 6 | 4 | 4 | 0 | 0 |
| MEAN: | 2.33 | 2.00 | — | — |
| SUM: | — | — | −2 | 2 |
| T= | | | | −1.58** |

*Suppressant suppressed hunger . . . True
**Confidence level for this conclusion below 90%

On the basis of the data presented above in Tables II–XIII, and in accordance with the invention, 2-acetylpyridine, eucaliptol, camphor and isopropylquinoline are preferred for suppressing appetite in an individual having appetite. These substances can be used individually or in combination.

The twelve suppressants and solvents tested are FDA-approved for inhalation in the concentrations disclosed. These odorants were selected from the FDA-approved Gras list.

What has been described herein is a novel appetite suppressant. While the suppressant of the present invention has been described with reference to a preferred device for application thereof, the invention is not limited to such an applictor. On the contrary, alternatives, changes or modifications may become apparent to those skilled in the art upon reading the foregoing description. Accordingly, such alternatives, changes or modifications are to be considered as forming a part of the invention insofar as they fall within the spirit and scope of the appended claims.

I claim:

1. A method of appetite suppression which comprises administration by inhalation to a person in need thereof, a volatile appetite suppressant composition comprising an effective amount 2-acetylpyridine.

2. The method of claim 1 wherein said composition includes an effective amount of a volatile solvent for selectively controlling the odor intensity and rate of volatilization of said suppressant into air.

3. The method of claim 2 wherein said solvent is dipropylene glycol.

4. The method of claim 3 wherein said suppressant has an odor intensity range substantially matching from about 10–500 ppm (volume/volume) of 1-butanol.

5. An appetite suppressant for humans comprising as appetite suppressant 2-acetylpyridine diluted in an effective amount of dipropylene glycol solvent for controlling the odor intensity and rate of volatilization of said 2-acetylpyridine into air.

* * * * *